(12) United States Patent
Hug et al.

(10) Patent No.: US 10,314,776 B2
(45) Date of Patent: Jun. 11, 2019

(54) DENTAL CARE PRODUCT FOR TOOTH WHITENING

(71) Applicant: CREDENTIS AG, Windisch (CH)

(72) Inventors: Michael Hug, Zofingen (CH); Dominikus Amadeus Lysek, Windisch (CH); Karl-Heinz Kunzelmann, Erding (DE)

(73) Assignee: Credentis AG, Windisch (CH)

( * ) Notice: Subject to any disclaimer, the term of this patent is extended or adjusted under 35 U.S.C. 154(b) by 41 days.

(21) Appl. No.: 14/916,494

(22) PCT Filed: Sep. 25, 2014

(86) PCT No.: PCT/EP2014/070487
§ 371 (c)(1),
(2) Date: Mar. 3, 2016

(87) PCT Pub. No.: WO2015/044268
PCT Pub. Date: Apr. 2, 2015

(65) Prior Publication Data
US 2016/0199283 A1    Jul. 14, 2016

(30) Foreign Application Priority Data

Sep. 25, 2013  (EP) .................................... 13185928
Aug. 8, 2014   (EP) .................................... 14180365

(51) Int. Cl.
| | | |
|---|---|---|
| *A61K 8/24* | (2006.01) | |
| *A61K 8/69* | (2006.01) | |
| *A46B 11/00* | (2006.01) | |
| *A61C 15/04* | (2006.01) | |
| *A61K 8/64* | (2006.01) | |
| *A61Q 11/00* | (2006.01) | |
| *A61Q 11/02* | (2006.01) | |
| *A61K 8/02* | (2006.01) | |
| *A61K 8/19* | (2006.01) | |

(52) U.S. Cl.
CPC ............ *A61K 8/69* (2013.01); *A46B 11/0003* (2013.01); *A61C 15/041* (2013.01); *A61K 8/02* (2013.01); *A61K 8/19* (2013.01); *A61K 8/24* (2013.01); *A61K 8/64* (2013.01); *A61Q 11/00* (2013.01); *A61Q 11/02* (2013.01)

(58) Field of Classification Search
None
See application file for complete search history.

(56) References Cited

U.S. PATENT DOCUMENTS

| | | | |
|---|---|---|---|
| 5,009,898 A | 4/1991 | Sakuma et al. | |
| 6,548,630 B1 | 4/2003 | Zhang et al. | |
| 2005/0037948 A1 | 2/2005 | Reynolds | |
| 2008/0075675 A1 | 3/2008 | Reynolds | |
| 2008/0160091 A1 | 7/2008 | Kropf et al. | |
| 2008/0199431 A1 | 8/2008 | Capito et al. | |
| 2008/0226566 A1 | 9/2008 | Poth et al. | |
| 2010/0129298 A1* | 5/2010 | Sakuma .................. A61K 8/24 424/57 |
| 2010/0247457 A1 | 9/2010 | Anton et al. | |
| 2010/0247589 A1 | 9/2010 | Fahnestock et al. | |
| 2010/0297203 A1 | 11/2010 | Tancredi et al. | |
| 2011/0201541 A1 | 8/2011 | Takamura et al. | |
| 2012/0058066 A1 | 3/2012 | Nagai et al. | |

FOREIGN PATENT DOCUMENTS

| | | |
|---|---|---|
| CN | 101385856 A | 3/2009 |
| EP | 0786245 A1 | 1/1997 |
| EP | 1 762 215 A1 | 3/2007 |
| EP | 2 327 428 A2 | 6/2011 |
| JP | 1017449 A | 1/1998 |
| JP | 115722 A | 1/1999 |
| JP | H115722 A | 1/1999 |
| JP | 2001122748 A | 5/2001 |
| JP | 2001131041 A | 5/2001 |
| JP | 2008081424 A | 4/2008 |
| JP | 20070176862 A | 1/2009 |
| WO | 2004007532 A1 | 1/2004 |
| WO | 2004007532 A2 | 1/2004 |
| WO | 2006047315 A2 | 5/2006 |
| WO | 2006073889 A2 | 7/2006 |
| WO | 2007000979 A1 | 4/2007 |
| WO | 2007137606 A1 | 12/2007 |
| WO | 2008081424 A1 | 7/2008 |

(Continued)

OTHER PUBLICATIONS

JP 11-5722 translation (JP 11-5722 translation obtained from https://www4.j-platpat.inpit.go.jp/cgi-bin/tran_web_cgi_ejje?u= on Mar. 24, 2017, 5 pages).*

(Continued)

*Primary Examiner* — Karlheinz R. Skowronek
*Assistant Examiner* — Ronald T Niebauer
(74) *Attorney, Agent, or Firm* — Thomas|Horstemeyer, LLP

(57) ABSTRACT

The present invention relates to the field of dental care, in particular, to a dental care product such as toothpaste (dentifrice), prophylactic paste, tooth powder, tooth polish, tooth gel, chewing gum, candy, lozenge, mouthwash, whitening strip, coated dental floss, coated toothbrush, paint-on gel, varnish, veneer, and tube, syringe or dental tray comprising a gel or paste, mouthwash, whitening strips and trays for whitening teeth, wherein the product comprises mineral particles such as crystals and a compound, preferably, a protein capable of forming a matrix which is a hydrogel, wherein the product comprises a fluorophore. The mineral particles may comprise, e.g., calcium phosphate, preferably, hydroxyapatite, preferably, in crystalline form. The protein matrix may comprise, e.g., a self-assembling peptide. The product also comprises a fluorophore, which may be a fluorescent amino acid residue of the protein matrix. The invention also relates to cosmetic use of the dental care product for whitening teeth or for use in treatment of a sensitive tooth or sensitive teeth and/or in prevention or treatment of caries, as well as a related method for tooth whitening.

Figure 1A:
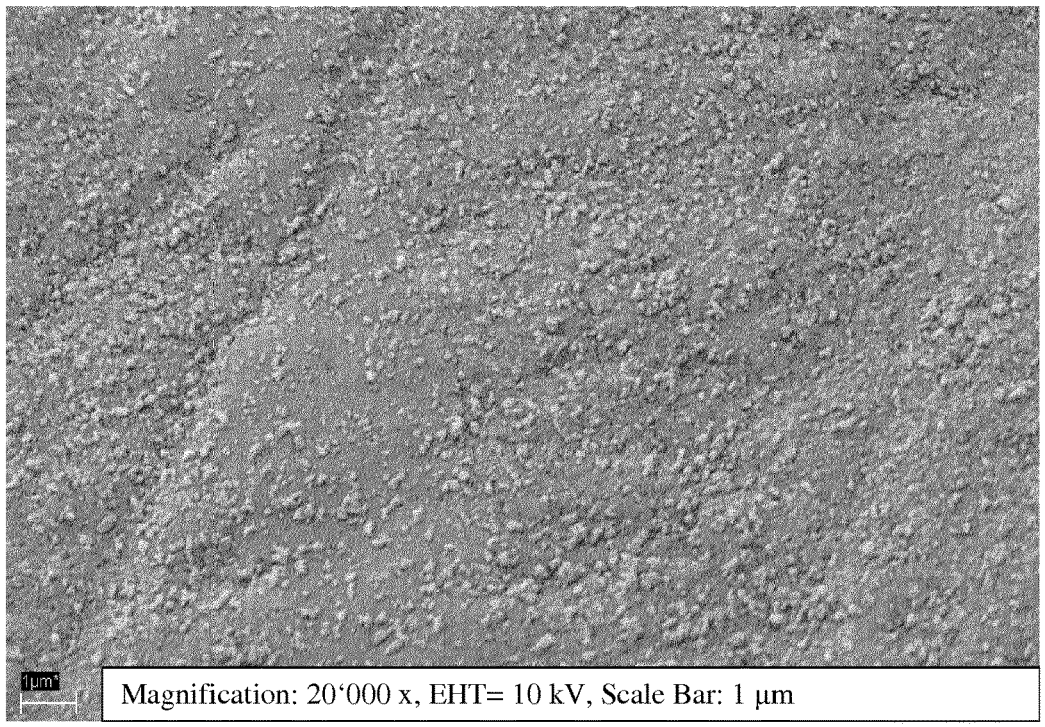

12 Claims, 2 Drawing Sheets
Specification includes a Sequence Listing.

(56) References Cited

FOREIGN PATENT DOCUMENTS

| WO | 2008113030 A2 | 9/2008 |
|---|---|---|
| WO | 2009026729 A1 | 3/2009 |
| WO | 2010041636 A1 | 4/2010 |
| WO | 2010103887 A1 | 9/2010 |
| WO | 2013068020 A1 | 5/2013 |

OTHER PUBLICATIONS

Balboaca et al. ('Amino acids sequence analysis on collagen' Bulletin USAVM-CN v63-64 2007 pp. 311-316).*
Blast search results for SEQ ID No. 1 (retrieved from https://blast.ncbi.nlm.nih.gov/Blast.cgi on May 25, 2017, 8 pages).*
PubMed abstract (retrieved from https://www.ncbi.nlm.nih.gov/pubmed/23841792 on May 25, 2017, 2 pages).*
Dabanoglu et al. 2009 Am J Dent 22:23-29.
Dahl et al. 2003 Grit Rev Oral Biol Med 14(4):292-304.
Delfino et al. 2009 J Appl. Oral Sci 17(4):284-8.
Demarco et al. 2009 Braz Oral Res. 23 Suppl 1:64-70.
Gerlach et al. 2002 Am J Dent. 15 Spec No. 7A-12A.
Jiang et al. 2008 J Dent 36(11):907-914.
Jin et al. 2013 Eur I Oral Sci 121:382-388.
Lim et al. 2009 Biomed Mater 4(2):025017.
Mohd et al. 2007 Biomed Mater Eng 17(2):69-75.
Niwa et al. 2001 J Mater Sci Mater Med 12:277-281.
Raoufi, S. and D. Birkhed 2010 Int Dent J60(6):419-423.
Roveri, Battistelli et al. 2009 J Nanomaterial, special issue, Article ID 746383.
International Search Report, issued in International Application No. PCT/EP2014/070487, dated Dec. 5, 2014.
International Written Opinion, issued in International Application No. PCT/EP2014/070487.
Kirkham et al., Self-assembling Peptide Scaffolds Promote Enamel Remineralization, Journal of Dental Research pp. 426-430, 2011.
First Office Action issued by the Japanese Patent Office for Application No. 2016-516598, dated Sep. 18, 2018.
Jin et al., Efficacy of Tooth Whitening with Different Calcium Phosphate-Based Formulations, European Journal of Oral Sciences, p. 382-388, 2013.

* cited by examiner

DENTAL CARE PRODUCT FOR TOOTH WHITENING

The present invention relates to the field of dental care, in particular, to a dental care product such as toothpaste (dentifrice), prophylactic paste, tooth powder, tooth polish, tooth gel, chewing gum, candy, lozenge, mouthwash, whitening strip, coated dental floss, coated toothbrush, paint-on gel, varnish, veneer, and tube, syringe or dental tray comprising a gel or paste, mouthwash, whitening strips and trays for whitening teeth, wherein the product comprises mineral particles such as crystals and a compound, preferably, a protein capable of forming a matrix which is a hydrogel, wherein the product comprises a fluorophore. The mineral particles may comprise, e.g., calcium phosphate, preferably, hydroxyapatite, preferably, in crystalline form. The protein matrix may comprise, e.g., a self-assembling peptide. The product also comprises a fluorophore, which may be a fluorescent amino acid residue of the protein matrix. The invention also relates to cosmetic use of the dental care product for whitening teeth or for use in treatment of a sensitive tooth or sensitive teeth and/or in prevention or treatment of caries, as well as a related method for tooth whitening.

Enamel of teeth is the hardest substance of the human body. It is composed of about 98% hydroxyapatite, a crystalline form of calcium phosphate, and some organic components. A thin layer of enamel forms on the surface of teeth with dentin as a base. Enamel is tougher and suitable for absorbing the stress of mastication without fracture. Dentin also comprises hydroxyapatite, with a higher porosity, and a higher content of organic structure.

Both extrinsic and intrinsic reasons contribute to discoloration of teeth. For example, coffee, tea, wine, carrots, oranges or tobacco can leave stains on the enamel surface. Certain antibiotics, excessive fluoride uptake or hereditary diseases can cause intrinsic discoloration. Tooth discoloration can be an important aesthetic problem for dental patients. For example, in the UK, around 20% of people are dissatisfied with their teeth colour. In the USA, 34% seem to be dissatisfied.

Often, superficial stains can be removed by thorough cleaning of teeth by the patient or a health professional. Polishing with abrasive material is sometimes used to this end, for example employing pastes which comprise particles of calcium phosphate, chalk, pumice or silica. If the patient desires a further more intrinsic reduction in teeth discoloration, chemical bleaching is the classical option. Various bleaching techniques are known, which are based upon an oxidizing agent such as peroxide. Bleaching can be performed by a health professional in a dental clinic or by the patient at home. For this, prescription products for overnight bleaching or bleaching toothpastes can be used.

However, in recent years, awareness of side effects associated with bleaching, such as demineralisation, erosion and tooth sensitivity caused by peroxides, has increased (e.g., Dahl et al., 2003). It has been suggested to use hydroxyapatite nanocrystals to remineralize tooth surfaces damaged e.g., by bleaching (Mohd et al., 2007, Jiang et al., 2008, Lim et al., 2009, Roveri et al., 2009). Hydroxyapatite crystalline particles, which closely mimic the natural material of the tooth, can be deposited on the tooth enamel. In addition to filling in scratches or eroded parts of a tooth, and prevention or treatment of caries, deposited hydroxyapatite can counteract hypersensitivity of teeth caused by exposition of dentin tubule upon recession of gums (WO 2007/137606 A1).

Amorphous Calcium Phosphate stabilised with phosphoproteins such as caseinphosphopeptide (CPP-ACP) has been used in oral care products for preventing and treating caries lesions (z.B. US 20050037948 A1, US 20080075675 A1, US 20100297203 A1).

It was found that calcium phosphate such as hydroxyapatite in particulate form also has whitening properties independent of bleaching or polishing (Niwa et al., 2001, Dabanoglu et al, 2009). Dabanoglu et al. compared different materials, e.g., nano-hydroxyapatite or nano-tricalcium phosphate or a dissolvable polymer film (methacrylic acid-ethyl acrylate copolymers) comprising nano-hydroxyapatite with regard to their whitening properties. They achieved a colour change, measured spectrometically as $\Delta E$ (L*a*b scale), with all tested materials. Measurement can be performed according to ISO 28399. The effect increased with three applications to a $\Delta E$ of about 3, which decreased with some materials after subjecting the treated teeth to shear force. It is noted that the average casual viewer can notice the difference between two colours that are 3-4 $\Delta E$ apart. A trained eye can differentiate between two colours that are 2-3 $\Delta E$ apart. Thus, while a perceivable change could be generated, there is still room for improvement.

WO 2013/068020 discloses a dental care product comprising hydroxyapatite having a surface functionalized with lactoferrin. This is suggested to form a thin film on the enamel surface, which improves teeth remineralisation and has an antibacterial effect.

JPH115722 relates to an aqueous composition for oral cavity cleaning, i.e., a mouthwash, which comprising hydroxyapatite particles. JP2008/081424 describes whitening of teeth by a composition comprising lactoferrin and lactoferrin decomposition product and cyclic or annular polyphosphates. JP 2007/0176862 describes use of a composition comprising hydrolysed silk and precipitates calcium carbonate for suppression of the elution of dentine and for caries prevention. JP 2001/131041 describes an oral composition such as a toothpaste comprising hydroxyapatite with improved storage stability, which comprises a magnesium salt. CN101385856 relates to a nanometer hydroxyapatite material used for absorbing and sustained release of muraminidase (lysozyme) for treatment/prevention of dental caries.

US 20100247589 A1 describes an oral care system with different components such as a monomeric peptide with a part binding to oral surfaces and a second binding element and a composition which may comprise particles which may bind to the second binding element and which comprise a benefit agent such as a whitening agent, e.g., $TiO_2$ or hydroxyapatite particles, or an anti-stain agent or enzyme. The peptide is suggested to facilitate binding of the benefit agent to the oral surface. US 2010/0247457 A1 also teaches peptide-based reagents comprising at least one tooth surface binding peptide for delivery of at least one polymer-coated white colorant to the surface of the teeth. Raoufi et al., 2010, have compared a commercial over the counter calcium peroxide toothpaste and a hydroxyapatite toothpaste (intended for bleaching or whitening teeth, respectively) with a fluoride placebo toothpaste, and found no objective whitening effect for any of the toothpastes in a 12 week clinical trial.

There is a need in the art for a dental care product effective in tooth whitening, which preferably minimizes disadvantages of bleaching such as demineralisation and tooth sensitivity, which is safe, preferably, for commercial over the counter sale, and which can be administered by the patient or consumer.

This problem was addressed by the present inventors. The invention provides a dental care product and its uses as described in the claims. In particular, the invention provides a dental care product comprising 0.4-60 wt %, preferably, 0.5-50 wt %, 1-40 wt %, 5-30 wt % or 10-25 or 15-20 wt %, e.g., 20-30 wt % or about 25 wt % mineral particles, the particles having a size of 10 nm-50 μm, and 0.001-5 wt %, preferably, 0.02-2 wt %, 0.04-1 wt %, 0.05-0.5 wt %, 0.05-0.2 wt % of an organic compound capable of forming an organic matrix, preferably, a protein capable of forming a protein matrix, e.g., a self-assembling peptide. The protein matrix is a hydrogel. The dental care product comprises a fluorophore.

The inventors surprisingly found that, by mixing mineral particles with a suitable organic matrix such as a suitable protein matrix in a dental care product according to the invention, the previously described whitening effect of hydroxyapatite particles on teeth can be significantly increased. The protein alone also does not achieve comparable effects, and the combination works in a synergistic manner. In particular, the invention provides a dental care product capable of producing a difference in whiteness of a tooth, measured on CIELAB (=L*a*b*) scale, of ΔE of more than 5 after 3 applications, preferably, ΔE of more than 5 after 1 application.

In the context of the present invention, the protein is capable of forming a protein matrix or hydrogel, in particular, through self-assembly. Preferably, the protein matrix is present in the dental care product in the form of a hydrogel, i.e. the proteins (e.g., self-assembling peptides), are not present as monomers. The term protein in the context of the invention relates to a protein comprising more than 100 amino acids and/or a peptide having 7-100 amino acids. The protein may comprise natural and/or non-natural amino acid residues such as ornithine. Preferably, the protein of the invention is selected from the group comprising amelogenin, serum albumin (preferably, bovine serum albumin or human serum albumin), lysozyme, a self-assembling peptide, a supramolecular assembly, and members of the collagen protein family (preferably, type I collagen, in particular, human or bovine collagen), e.g., in the form of gelatine, or other proteins rich in aromatic-residues (e.g., comprising more than 10% or more than 20% of aromatic residues). All of these proteins are known to be capable of forming a hydrogel.

The inventors have shown that a matrix of said protein and the mineral particles on the tooth surface can be formed, which has an increased whitening effect compared to the layer of mineral particles deposited on the tooth surface with previous methods (e.g., Dabanoglu et al, 2009). The structures incorporating the mineral particles of the present invention are believed to be preformed in the dental care product and stable under oral conditions. They are also at least partly resistant to brushing with an ultrasound toothbrush.

Self-assembling peptides are preferred proteins of the invention. Self-assembling peptides are provided, e.g., in WO 2004/007532 A1, which is fully incorporated herein by reference. WO 2004/007532 A1 discloses peptides that are capable of forming three-dimensional scaffolds, thereby promoting nucleation of de-novo calcium phosphate. These artificial peptides assemble in one dimension to form beta-sheet, and higher order assemblies such as tape-like assemblies. Three-dimensional supramolecular structures of self-assembling proteins can be formed, which have an affinity for/to calcium phosphate.

Several other self-assembling peptides (SAP) which may be employed have been described in the prior art. For example, WO 2010/041636 A1 describes a bioadsorbable peptide tissue occluding agent containing an artificial peptide having 8-200 amino acid residues with the hydrophilic amino acids and hydrophobic amino acids alternately bonded, which self-assembles into a beta-structure at physiological pH. Self-assembling peptides with alternating hydrophobic and hydrophilic residues or stretches which interact with the extracellular matrix are also disclosed in WO 2008/113030 A2. WO 2010/103887 A1 discloses self-assembling peptides, which comprise basic, hydrophobic and acidic amino acids of a specific primary sequence and peptide gels thereof which have high strength. WO2010/019651 A1 relates to other self-assembling peptides.

Another application, WO 2007/000979 A1, describes self-assembling peptides with polar and non-polar amino acids. The peptides are capable of forming a beta-sheet structure in which the non-polar amino acid residues are arranged on one side of the structure in the assembled form. Amphiphilic self-assembling peptides for use as stable macroscopic membranes, which are used in biomaterial applications, such as slow-diffusion drug delivery, are described in U.S. Pat. No. 6,548,630.

EP 2 327 428 A2 refers to a pharmaceutical composition comprising self-assembling peptide nanofibers, which are complementary to each other, and at least one cell for repairing damaged tissue, such as tissue after a myocardial infarction.

In the context of the present invention, self-assembling peptides taught in WO 2004/007532 A1 are specifically preferred. Most preferably, said protein is the self-assembling peptide designated oligopeptide 104 (SEQ ID NO: 1, QQRFEWEFEQQ) or the self-assembling peptide having SEQ ID NO: 2, QQOFOWOFQQQ, or it comprises said peptide. It may also be a self-assembling peptide having at least 60% sequence identity to a peptide consisting of SEQ ID NO: 1, 2, 3, 4, 5, 6, 7, 8, 9, 10, 11, 12, 13, 14, 15, 16, 17, 18 or 19. Preferably, the peptide has at least 70%, at least 80%, or at least 90% sequence identity to a peptide consisting of SEQ IDs, preferably, SEQ ID NO: 1 or SEQ ID NO: 2. Most preferably, the peptide has at least 60%, at least 70%, at least 80%, or at least 90% sequence identity to a peptide consisting of SEQ ID NO: 1 or is said peptide. Alternatively, the peptide may have at least 60%, at least 70%, at least 80%, or at least 90% sequence identity to a peptide consisting of SEQ ID NO: 2 or be said peptide. Examples of self-assembling peptides that may be employed in the invention are provided in Table 1 below. Self-assembling peptides may be modified peptides, comprising an Ac-N-terminus and/or NH2-C-Terminus, or non-modified peptides.

TABLE 1

| SEQ ID NO | sequence |
| --- | --- |
| SEQ ID NO: 1 | QQRFEWEFEQQ |
| SEQ ID NO: 2 | QQOFOWOFQQQ |
| SEQ ID NO: 3 | QQRFOWOFEQQ |
| SEQ ID NO: 4 | QQRFQWQFEQQ |
| SEQ ID NO: 5 | QQEFEWEFEQQ |
| SEQ ID NO: 6 | QQOFOWOFOQ |

TABLE 1-continued

| SEQ ID NO | sequence |
|---|---|
| SEQ ID NO: 7 | EQEFEWEFEQE |
| SEQ ID NO: 8 | QQEFEWEFEQQ |
| SEQ ID NO: 9 | ESEFEWEFESE |
| SEQ ID NO: 10 | QQOFOWOFOQQ |
| SEQ ID NO: 11 | OQOFOWOFOQO |
| SEQ ID NO: 12 | SSOFOWOFOSS |
| SEQ ID NO: 13 | SSRFEWEFESS |
| SEQ ID NO: 14 | SSRFOWOFESS |
| SEQ ID NO: 15 | QQOFOWOFOQQ |
| SEQ ID NO: 16 | NNRFEWEFENN |
| SEQ ID NO: 17 | NNRFOWOFENN |
| SEQ ID NO: 18 | TTRFEWEFETT |
| SEQ ID NO: 19 | TTRFOWOFETT |

To be able to bind the mineral particles on a tooth surface, the matrix has to be able to bind the mineral particles and adhere to the tooth surface. The matrix thus comprises binding sites for the mineral particles which enable it to bind the particles, which preferably comprise calcium, on the tooth surface. For example, charged amino acid residues such as Glu or Orn on the surface of self-assembling peptides bind to hydroxyapatite particles and to the tooth surface, which is also substantially formed of hydroxyapatite. Without intending to be bound by the theory, it is believed that both reactions increase the stability of the formed complex to generate a more permanent whitening effect. A capability for three-dimensional self-organization, which is e.g., found in collagen, supramolecular assemblies or in self-assembling peptides, is important for binding. In general, highly charged surfaces will promote adhesion of the mineral particles. The protein-matrices work particularly well when their surface shows glutamate or ornithine residues which may attach to calcium phosphate or to other mineral particles. Preferably, the protein comprises 5% or more, 10% or more, 20% or more or 30% or more charged amino acid residues, such as glutamate and/or ornithine residues.

The dental care product comprises a fluorophore. Trp is a preferred fluorophore. Preferably, said fluorophore is an amino acid residue of the protein matrix, preferably Trp, Tyr and/or Phe. Preferably 5% or more, 10% or more, 20% or more or 30% or more of the residues of the matrix protein are Trp, Tyr and/or Phe. Most preferably, 5% or more, 10% or more, 20% or more or 30% or more of the residues of the matrix protein are Trp.

In one embodiment, the protein comprises 5% or more, 10% or more, 20% or more or 30% or more charged amino acid residues such as glutamate and/or ornithine, and the protein comprises 5% or more, 10% or more, 20% or more or 30% or more fluorescent amino acid residues such as Trp.

In an alternative embodiment, the dental care product comprises a fluorophore that is no amino acid residue of the protein, and which in one embodiment is not covalently bound to the matrix. Covalent linkage of a fluorophore to the protein is also envisioned. For example, the fluorophore may be a derivative of phthalocyanine, e.g., copper phthalocyanine (covarin blue). Embedding such a fluorophore into the combination of matrix and mineral particles as described above surprisingly leads to a more permanent and more intense whitening effect compared to incorporation of such fluorophores into a conventional toothpaste. Of course, the dental care product may also comprise both a fluorophore that is an amino acid residue of the protein and an additional fluorophore that is not. However, surprisingly, addition of a fluorophore to a dental care product of the invention is not required to achieve the whitening effect, if the protein comprises a fluorescent amino acid residue as described above.

The mineral particles preferably comprise calcium phosphate or consist thereof. Calcium phosphate may, in the context of the present invention, be monocalciumphosphat-monohydrate (MCPM) $Ca(H_2PO_4)_2 \cdot H_2O$, monocalciumphosphate anhydrate (MCPA) $Ca(H_2PO4)_2$, dicalciumphosphate dihydrate (DCPD, Brushit), $CaHPO_4 \cdot 2H_2O$, dicalciumphosphate anhydrate (DCPA, Monetit) $CaHPO_4$], Octacalciumphosphate (OCP) $Ca_8(HPO_4)_2(PO_4)_4 \cdot 5H_2O$, α-tricalciumphosphate (α-TCP) $\alpha\text{-}Ca_3(PO_4)_2$, β-tricalciumphosphate (β-TCP) $\beta\text{-}Ca_3(PO_4)_2$, amorphous calcium phosphate (ACP) $Ca_x(PO_4)_y \cdot nH_2O$, calcium-deficient hydroxyapatite (CDHA) $Ca_{10}\text{-}x(HPO_4)_x(PO_4)_6\text{-}x(OH)_{2-x}$ (0<x<1), hydroxyapatite (HA) $Ca_{10}(PO_4)_6(OH)_2$, or tetracalciumphosphate (TTCP) $Ca_4(PO_4)_2O$), or a mixture of different calcium phosphates. In one embodiment, the particles or have a degree of crystallinity of 40% or more, e.g., 40-60%, 60% or more, 80% or more or 90% or more, or they are crystals. A higher degree of crystallinity is expected to make the effect on whiteness of teeth more long-lasting. Throughout the invention, the calcium phosphate preferably is hydroxyapatite. The hydroxyapatite may be substituted hydroxyapatite e.g., carbonate hydroxyapatite and zinc carbonate hydroxyapatite, or pure calcium phosphate, preferably, in crystalline form. In the context of the invention, reference to calcium phosphate or hydroxyapatite includes reference to derivatised calcium phosphates or hydroxyapatites of this kind unless otherwise mentioned. Of course, the calcium phosphate or hydroxyapatite may also consist of $CaPO_4$ (and of course crystal water as appropriate for the respective crystal form) only. The mineral may also be a bioglass (comprising acid soluble Calcium silicates), Kaolin $(Al_2Si_2O_5(OH)_4)$ or $TiO_2$ in its different crystal forms.

The hydroxyapatite particles may be obtained according to methods disclosed, e.g., in Roveri, Battistelli et al., 2009, EP 1 762 215 A1, US 20050037948 A1, US 20080075675 A1, US 20100247589 A1, US 20100297203 A1, WO 2007/137606 A1, or WO 2013/068020 A1. Preferably, the hydroxyapatite is obtainable according to WO 2007/137606 A1 and can be commercially obtained from Budenheim, Budenheim, Germany.

The size of the mineral particles preferably is measured by granulometry, e.g., with a light scattering particle size distribution analyzer (such as LA-950, Horiba, Kyoto, Japan). The form of the crystals preferably is needle-shaped, but it may also be rod-shaped or acicular.

The size of the particles is 10 nm-50 μm, preferably, 0.1 μm-25 μm, more preferably 1-25 μm, 4-20 μm or 5-15 μm, 8.12 μm or about 10 μm. In one embodiment, the size is 10-1200 nm. In the context of the invention, this means that at least 80%, preferably, at least 90% of particles, at least 95% or 100% of the particles have the respective size.

In one embodiment, 30-100% or 50-90% of particles have a size of 200-600 nm. This size was selected for the experiments as it is corresponds to the wavelength of UV light or visible light, which plays an important role in white appearance of teeth. In the context of the invention, "about" means +/−10%, preferably, +/−5%.

In one embodiment, the particles have a mixture of different sizes, which may provide a still more intense whitening effect. In particular, for example 30-70% of particles may have a size of 200-400 nm, 30-70% of particles have a size of 400-600 nm, and, optionally, 30-70% of particles have a size of 10-200 nm. Alternatively, for example, 30-70% of particles may have a size of about 10-15 µm, about 30-70% of particles have a size of about 4-10 µm and, optionally, about 10-40% of particles have a size of 0.1-4 µm (all referring to wt %).

In a preferred embodiment, the protein is a self-assembling peptide, and the fluorophore is an amino acid residue of the self-assembling peptide, preferably, Trp, and the particles, which preferably are hydroxyapatite particles have a size of 1-25 µm, preferably, 4-20 µm.

The dental care product is selected from the group comprising toothpaste (dentifrice), prophylactic paste, tooth powder, tooth polish, tooth gel, chewing gum, candy, lozenge, mouthwash, whitening strip, paint-on gel, varnish, veneer, and tube, syringe or dental tray comprising a gel or paste, or a gel or paste coated on an application support such as dental floss or a toothbrush (a manual, electric, sound, a combination thereof or ultrasound toothbrush). The toothpaste can be a toothpaste for a conventional toothbrush, but it can also be a toothpaste for an ultrasonic toothbrush. In one embodiment, the dental care product is not a liquid, but a paste or gel, most preferably, it is a toothpaste or a tooth gel comprising 0.5-40 wt % of said mineral particles and 0.02-1 wt %. preferably, 0.05-0.5 wt % of said organic matrix, preferably, protein matrix. A gel is a non-fluid colloidal network or polymer network that is expanded throughout its whole volume by a fluid. In the case of a hydrogel, the fluid is water. In contrast to a liquid, a gel has a finite, usually rather small, yield stress.

The dental care product may additionally comprise one or more typical ingredients of the respective dental care product. Such typical ingredients may be:

abrasive agents such as carbonates, phosphates, silicates, acrylates, alumina, suspension agents such as glycerine, polyethylene glycols (PEG), sorbitol, xylitol, binding agents such as cellulose and derivate thereof, carrageenan, paraffin, xylose, detergents such as hydrogenated castor oil, sodium lauryl sulphate, aroma such as caramel, vanillin, menthol, conserving agent such as ethanol, sodium benzoate, colouring agents such as solvent red, acid blue 3, active agents such as fluorides, preferably, in the form of tertiary amines, such as amine fluoride or organic fluoride such as sodium monofluorophosphat, potassium nitrate, and/or oxalate.

In one embodiment of the invention, the product is a toothpaste comprising all or the main ingredients of Curodont™ Repair (i.e., Oligopeptide 104 (SEQ ID NO: 1) and a bulking agent) or, preferably, of Curodont™ Protect, (both available from credentis ag, Switzerland) and added mineral particles, in particular, calcium phosphate, preferably, hydroxyapatite particles and/or another crystalline form, most preferably, hydroxyapatite. Thus, ingredients may be, e.g., hydroxyapatite particles and/or calcium phosphate in another crystalline form, preferably, hydroxyapatite, and Curodont™ Protect, i.e., hydrogenated starch hydrolysate, aqua, hydrated silica, PEG-8; cellulose gum, sodium monofluorophosphate, aroma, sodium saccharin, citric acid, sodium hydroxide, dicalcium phosphate, oligopeptide-104, calcium glycerophosphate, sodium chloride, sodium sulfate, limonene, cinnamal, and CI 42090.

In one embodiment, the product is a toothpaste comprising about 50% Curodont™ Protect, about 25% hydroxyapatite particles and about 25% water.

The present invention also relates to cosmetic use of the dental care product of the invention for tooth whitening. A method of tooth whitening for cosmetic reasons is also disclosed, comprising administering the dental care product of the invention to a tooth. In the context of the invention, unless explicitly mentioned or clear from the context, "a" is not limited to the singular, but can also mean "one or more". For example, reference to "a tooth" includes the option that more than one tooth, in particular, all teeth of one person, are designated. The dental care product of the invention may also be used for whitening crowns, implants, filling materials and other oral appliances.

In the method of the invention, the composition is preferably administered one, two or three times a day on 1, 2, 3, 4, 5, 6, 7 or more days, in one embodiment, daily. It can also be administered less often, e.g., once a week or once a month. Frequency of administration is strongly dependent on the whitening effect desired by the user, as well as on the amount of mechanical abrasion to which the teeth are subjected. This includes life-long administration, preferably starting after the permanent teeth have erupted, in particular, after discoloration of a tooth has been noticed. Administration means that a tooth, or, preferably, all teeth of a person are contacted with the dental care product in the way this respective type of product is typically used. For example, a toothpaste is typically used to brush teeth for a time of 1-5 minutes, in particular, about 2-3 minutes.

As the dental care product of the invention does not lead to the undesired side effects of bleaching products comprising peroxides, it can be used daily for all cycles of dental care without harm to the teeth or the gums. As the dental care product may further enhance remineralisation of teeth, reduce tooth sensitivity and prevents caries, and may even be used to treat beginning caries lesions, no additional dental care product is required. Additionally, the product can be used to inhibit the demineralisation of teeth. In particular, the dentifrice or toothpaste of the invention may be used for every brushing of teeth.

Alternatively, it may be used in addition to or alternately with a different dentifrice, e.g., an alternative fluoride containing toothpaste. For example, an alternative fluoride containing toothpaste may be used in the mornings, and the toothpaste of the invention may be used in the evening after the last meal of the day. The dental care product may also be used after normal dental care, e.g. in the evening after brushing teeth.

The present invention also provides the dental care product of the invention for use in treatment of a sensitive tooth and/or for prevention or treatment of caries. Also disclosed is a method of treating a sensitive tooth and/or of preventing and/or treating caries and/or tooth whitening comprising administrating an effective amount of the dental care product of the invention to a tooth or to teeth.

The following examples are intended to illustrate, but not to limit the invention. All literature cited in the present application is herewith incorporated herein in full.

LEGENDS

Figure 1B:
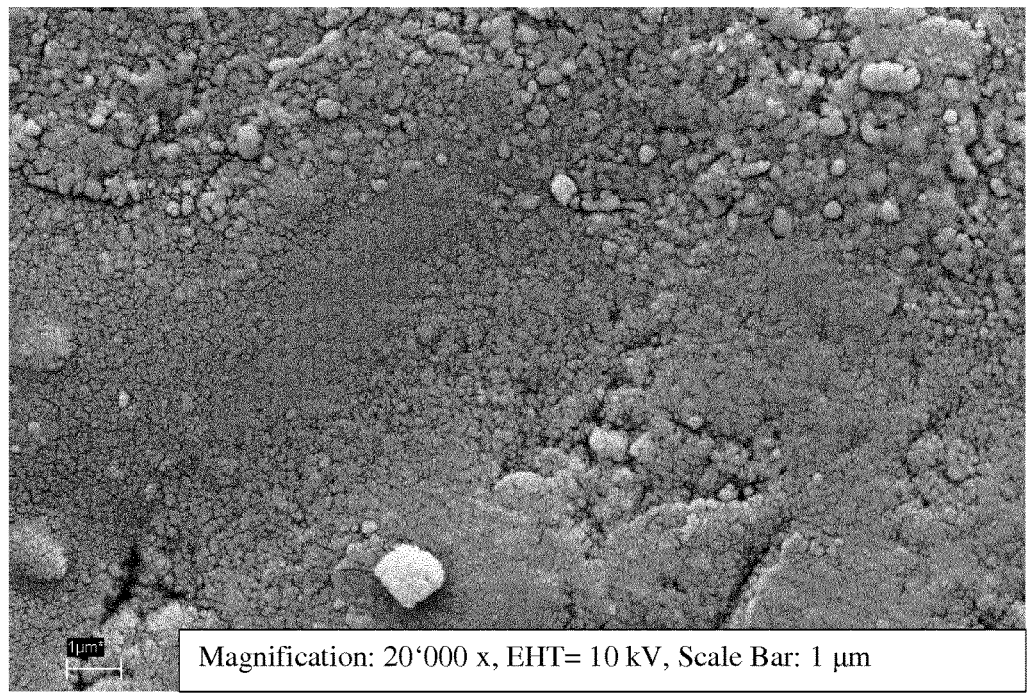

FIG. 1 (A) Electron microscopy picture of tooth surface treated with mixture of P11-4 matrix and hydroxyapatite particle suspension. The surface of the tooth shows tightly bound particles. (B) Electron microscopy picture of tooth surface treated only with hydroxyapatite particle suspension in water. The surface shows unregular positioning of particles on the surface.

Figure 2:
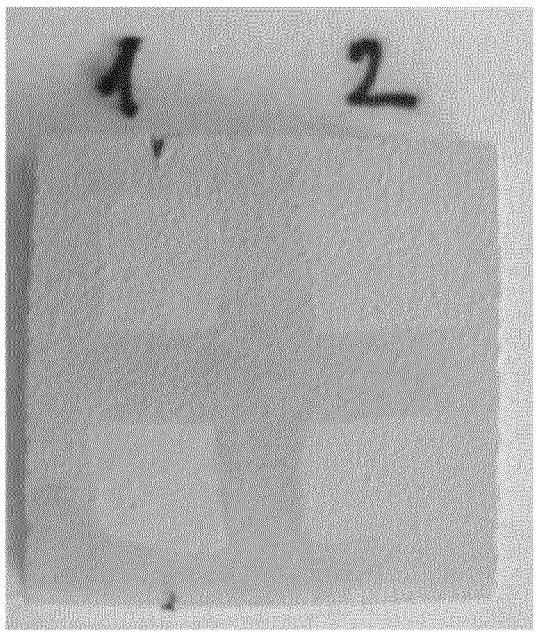
Figure 2:
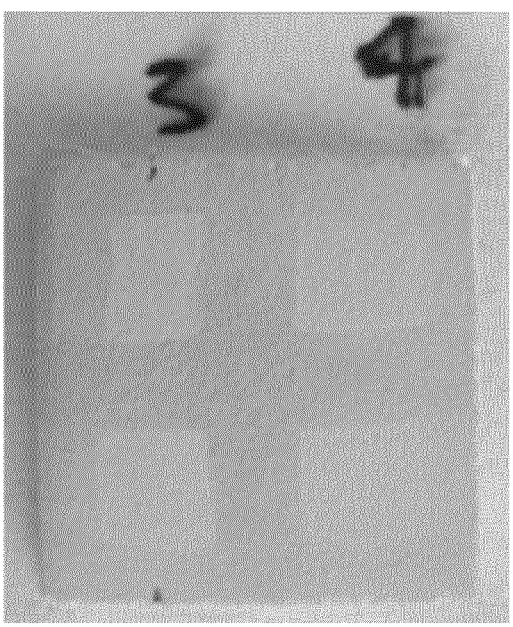
Figure 2:
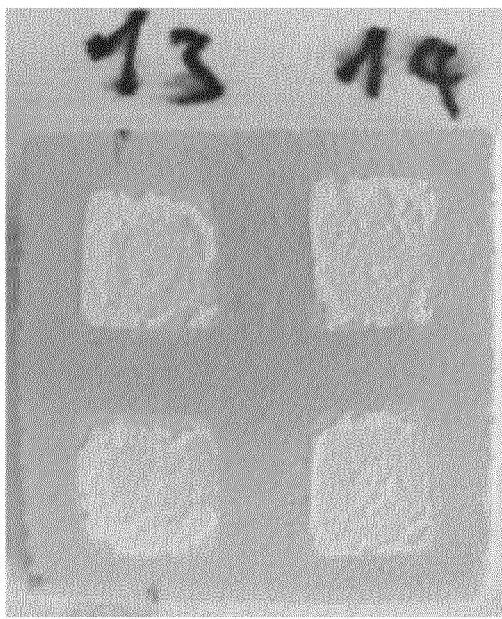
Figure 2:
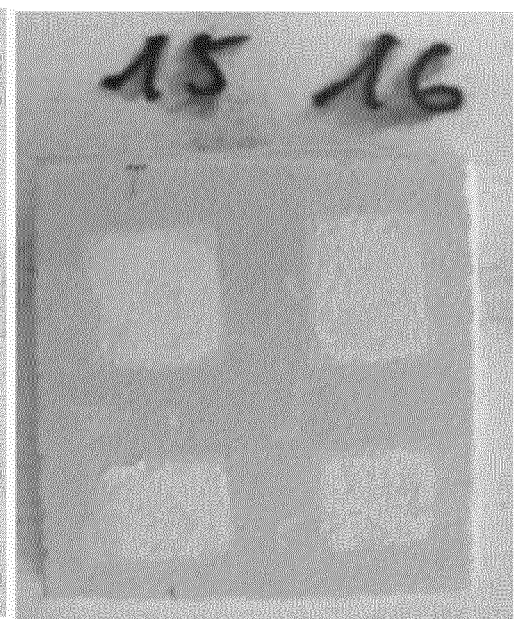

FIG. 2 Photographic assessment of the whitening effect of different hydroxyapatite particles on clay plates in the absence (1-4) and presence (1+-4+) of self-assembling peptide (Curodont™ Protect), according to the protocol of example 2. The pictures show the clay plates after brushing with a tooth brush.

EXAMPLES

Example 1

Materials and Methods

Suspensions of oligopeptide 104 (5 mg/ml) with or without hydroxyapatite particles (average size d50≤300 nm (Horiba); 40-60% crystallinity, 25 wt %) were generated.

The suspensions were directly applied onto an enamel surface of a tooth, and residues washed off (10 sec). The specimen was stored in distilled water for 24 hours at 37° C. The procedure was repeated 3 times.

The tooth colour was measured with a dental spectrophotometer (VITA Easyshade). The illumination conditions were standardized with a black box as the background for the teeth during the measurement. The tip was applied perpendicular to the tooth surface and the average L*a*b-values from three repetitions were used for evaluations. Colour measurement were done at baseline (t1=without treatment), 24 hours after first application (t1), 24 hours after second application (t3), 24 hours after the third application (t4).

The mean changes of the L*a*b-values between different measurements in each group were expressed as ΔE (according to ISO 28399).

Results

The results are provided in Table 2 below:

TABLE 2

|  | Control (HA only) | Test (HA + oligopeptide 104) |
|---|---|---|
| ΔE (t2-t1) - $1^{st}$ application | 2.3 | 4.6 |
| ΔE (t3-t2) - $2^{nd}$ application | 1.1 | 1.9 |
| ΔE (t4-t3) - $3^{rd}$ application | 1.5 | 0.6 |

The experiment shows that, surprisingly, the combination of a protein matrix according to the invention with HA significantly increases the whitening effect seen upon application of HA only.

Example 2

Test Protocol

1. A ceramic plate made from clay is divided into four compartments using colorless nail polish. All chemicals substances are weighed out and combined in a tube. The tube is filled with nanopure water ad 100% wt. If gelatin is used, the suspension is heated in a water bath by 80° C. during 5 minutes. Afterwards the suspension is mixed by a vortex mixer. The suspension is ready to be applied to the ceramic plate; this is done in two pipet steps by a volume of 50 μl. Between the two pipet steps a break of 10 minutes is done. The ceramic plate is dried for about 3 hours.

2. The ceramic plate is incubated in nanopure water for 24 hours. After the incubation, the ceramic plate is removed and left to dry.

3. The whiteness of the ceramic plate is measured by the Vita Easyshade spectrophotometer (Advance 4.0, SN: H26818, Vita Zahnfabrik GmbH, Bad Sackingen). Each field is measured three times and the average value used.

4. The described procedure (1-3) is repeated three times. The mean changes of the L*a*b*-values between different measurements in each group were expressed as ΔE which was calculated using the method according to ISO norm 28399:2011 (Products for external tooth bleaching).

5. After three applications, the ceramic plate is brushed by an ultrasonic toothbrush at a distance of 0.5 cm for 2 minutes. The Lab values of the plate are measured again, as described above.

Tested Materials

Different compositions according to the invention and to the prior art were tested according to the test protocol described above. % relates to wt/wt %. Water is added ad 100%. Curodont Protect™ comprises 1 mg/g Oligopeptide 104.

TABLE 3A

Compositions comprising different HA particles with or without self-assembling peptide/Curodont Protect ™

| No. | Powder | %[wt] | PS [μm] | Water %[wt] | Curodont Protect ™ %[wt] | SAP [w/w] |
|---|---|---|---|---|---|---|
| 1 | β-TCP sintered CAMCERAM 2 | 0.4 | 20 | 99.6 | — |  |
| 2 | α-TCP sintered CAMCERAM 2 | 0.4 | 20 | 99.6 | — |  |
| 3 | 50% HA + 50% β-TCP | 0.4 | 25/32 | 99.6 | — |  |
| 4 | 40% HA + 60% β-TCP | 0.4 | 25/32 | 99.6 | — |  |
| 1+ | β-TCP sintered CAMCERAM 2 | 0.4 | 20 | 92.9 | 6.7 | $6.7*10^{-3}$ |
| 2+ | α-TCP sintered CAMCERAM 2 | 0.4 | 20 | 92.9 | 6.7 | $6.7*10^{-3}$ |
| 3+ | 50% HA + 50% β-TCP | 0.4 | 25/32 | 92.9 | 6.7 | $6.7*10^{-3}$ |
| 4+ | 40% HA + 60% β-TCP | 0.4 | 25/32 | 92.9 | 6.7 | $6.7*10^{-3}$ |

TABLE 3B

Whithening effect of different HA particles with or without
self-assembling peptide/Curodont Protect ™· ΔE refers
to changes to baseline

| No. | ΔE 24 h after 1. Application* | ΔE 24 h after 2. Application* | ΔE 24 h after 3. Application* | ΔE 24 h after teeth brushing* |
|---|---|---|---|---|
| 1 | 1.8 | 4.2 | 3.4 | 3.0 |
| 2 | 1.0 | 3.4 | 2.0 | 1.7 |
| 3 | 1.8 | 4.3 | 3.0 | 3.0 |
| 4 | 2.1 | 3.7 | 2.5 | 3.5 |
| 1+ | 4.8 | 12.3 | 8.0 | 7.8 |
| 2+ | 5.8 | 11.1 | 8.1 | 7.4 |
| 3+ | 4.6 | 5.8 | 7.3 | 6.6 |
| 4+ | 3.6 | 5.2 | 6.2 | 6.8 |

*corrected by baseline

TABLE 4A

Compositions comprising different amounts of HA

| No. | Powder | %[wt] | PS [µm] | TWEEN %[wt] | Curodont Protect %[wt] | Glycerol %[wt] | Gelatin %[wt] | PEG %[wt] |
|---|---|---|---|---|---|---|---|---|
| NF1** | HA raw calcined 900° C./3 h | 0.5 | <10 | 0.1 | 2 | 27 | 0.5 | 30 |
| NF2** | HA raw calcined 900° C./3 h | 1 | <10 | 0.1 | 2 | 27 | 0.5 | 30 |
| NF3** | HA raw calcined 900° C./3 h | 2 | <10 | 0.1 | 2 | 27 | 0.5 | 30 |

TABLE 4B

Whithening effect of compositions
comprising different amounts of HA

| No. | ΔE 24 h after 1. Application* | ΔE 24 h after 2. Application* | ΔE 24 h after 3. Application* | ΔE 24 h after teeth brushing* |
|---|---|---|---|---|
| NF1 | 1.5 | 5.8 | 5.8 | 4.4 |
| NF2 | 1.8 | 7.8 | 8.6 | 6.6 |
| NF3 | 4.0 | 7.8 | 7.8 | 7.6 |

*corrected by baseline

The experiment demonstrates that different amounts of HA, together with self-assembling peptide, have a whitening effect, which is improved with a higher amount of HA.

TABLE 5A

Comparative compositions from the prior art;

31JP composition according to example 31 of JP2008/081424

8% lactoferrine,
2% lactoferrine hydrolysate,
43% glycerol,
23.5% polyethylenglycol (PEG),
15% silicic acid anhydride
5% hydroxyapatite 10 µm
3% sodium methylcellulose
0.3% sodium lauryl sulfate TABLE 5A-continued Comparative compositions from the prior art;

10JP composition according to example 10 of JPH115722 (mouth wash)

1% hydroxyapatite 1 µm
2% ascorbic acid
1% sodium ascorbate
0.5% collagen
0.5% gelatin/collagen decomposition product
10% glycerol
1% ethanol

TABLE 5B

Whithening effect of compositions according to the prior art

| No. | ΔE 24 h after 1. Application* | ΔE 24 h after 2. Application* | ΔE 24 h after 3. Application* | ΔE 24 h after teeth brushing* |
|---|---|---|---|---|
| 31JP | 0.7 | 3.0 | 2.3 | 1.2 |
| 10JP | 3.3 | 1.0 | 2.2 | 2.5 |

*corrected by baseline

The comparison with prior art compositions shows that the compositions of the present invention are surprisingly much more suitable for tooth whitening. In particular, it should be noted that after application, composition 31JP built up a thick crust, which, by itself, floated off during the 24 hour incubation in water. Composition 10JP turned to a yellow colour.

Example 3

A mono-centric uncontrolled cosmetic study with 40 volunteers desiring lighter/whiter teeth was carried out. The primary goal of the study was assessment of the whitening effect of the assessed product in vivo, using a dental spectrometer (VITA easyshade). Secondary goals were
a) assessment of safety and tolerability of the product,
b) identification and verification of application frequency of the product,
c) assessment of the durability of the whitening effect,
d) assessment of an additional effect of repeated application.
All subjects were between 18 and 75 years old. At least one tooth had to reach a brightness level of >=15 with VITA easyshade. The subjects had healthy incisors and canines of the upper jaw, i.e., free from buccal caries, no erosion, no partial restorations (said criteria applied for the at least one tooth which had to reach the brightness level of >=15 with VITA easyshade). The subjects further had to understand all procedures and be able and willing to follow the instructions, they had to agree to all measurements and controls, and they had to sign a corresponding declaration before the start of the study. Subjects with general sensibility to sugar, bad oral hygiene, fluorosis on the studied teeth, or subjects who took part in another clinical study or performed bleaching during the study were excluded.

The tested product consisted of 50% Curodont Protect™ (comprising 1 mg Oligopeptide 104/g Curodont Protect™, accordingly, the product contained 0.5 mg/g Oligopeptide 104, i.e., 0.05% of the self-assembling peptide), 25% hydroxyl apatite (d50≤300 nm (Horiba)) and 25% water).

On day 0, at a dental surgery, the dentist or a member of the study team applied the product to the teeth with a dental tray for upper and lower jaw, respectively. After 5-10 min, the subject spit out the product and flushed his/her teeth with water. On days 1-7, once daily, in the evening after regular toothcare, the subject brushed the frontal teeth for 1-2 minutes with the product. During the time of the study, the subjects were instructed to clean their teeth 2-3 times daily, as usual, using a fluoridated toothpaste, Candida Fresh®, and a electric toothbrush (Sonicare®).

Brightness of the at least one assessed tooth was recorded with the dental spectrometer before and after the first treatment (D0T), on day 1 (before contact with the product on that day) on day 7 (D7) (before contact with the product on that day) and on day 30 (D30). The mean changes of the L*a*b-values between different measurements in each group were expressed as ΔE (according to ISO 28399). Results are shown in Table 3 below.

TABLE 6

In vivo effects of tooth whitening according to the invention.
The table provides ΔE values in reference to the measurement before treatment, i.e., all values are corrected by baseline.

| Subject | D 0T | D 1 | D 7 | D 30 |
|---|---|---|---|---|
| 1 | 1.52 | 6.64 | 2.68 | 6.71 |
| 2 | 1.21 | 2.08 | 4.41 | 4.01 |
| 3 | 2.08 | 4.88 | 5.49 | 6.24 |
| 4 | 2.25 | 5.14 | 5.36 | 3.90 |
| 5 | 2.16 | 2.32 | 2.92 | 6.36 |
| 6 | 2.05 | 1.86 | 5.70 | 5.17 |
| 7 | 2.30 | 2.66 | 3.17 | 5.17 |
| 8 | 1.87 | 5.25 | 7.13 | 5.51 |
| 9 | 3.11 | 3.21 | 6.57 | 4.84 |
| 10 | 1.59 | 2.02 | 4.37 | 4.88 |
| 11 | 3.48 | 2.95 | 4.24 | 3.44 |
| 12 | 1.41 | 1.36 | 5.39 | 1.38 |
| 13 | 2.40 | 9.91 | 2.91 | 2.54 |
| 14 | 1.09 | 2.84 | 2.89 | 2.75 |
| 15 | 1.46 | 3.04 | 2.81 | 2.54 |
| 16 | 2.52 | 2.22 | 2.45 | 2.28 |
| 17 | 3.23 | 1.96 | 2.08 | 1.81 |
| 18 | 3.56 | 2.20 | 4.77 | 3.16 |
| 19 | 1.45 | 2.52 | 1.85 | 1.63 |
| 20 | 1.42 | 2.09 | 1.26 | 1.76 |
| 21 | 2.33 | 1.13 | 2.88 | 6.75 |
| 22 | 2.90 | 6.07 | 2.46 | 5.70 |
| 23 | 2.60 | 6.74 | 1.83 | 7.18 |
| 24 | 3.50 | 3.52 | 4.43 | 3.31 |
| 25 | 3.18 | 4.00 | 3.83 | 4.79 |
| 26 | 3.57 | 4.09 | 5.45 | 5.10 |
| 27 | 5.94 | 2.99 | 3.92 | ** |
| 28 | 3.55 | 2.60 | 3.05 | 3.81 |
| 29 | 4.50 | 4.68 | 4.23 | 3.19 |

TABLE 6-continued

In vivo effects of tooth whitening according to the invention.
The table provides ΔE values in reference to the measurement before treatment, i.e., all values are corrected by baseline.

| Subject | D 0T | D 1 | D 7 | D 30 |
|---|---|---|---|---|
| 30 | 3.77 | 3.00 | 5.61 | 1.92 |
| 31 | 3.10 | 2.49 | 6.69 | 2.87 |
| 32 | 3.75 | 1.98 | 6.85 | 2.37 |
| 33 | 1.77 | 2.73 | 4.63 | 3.72 |
| 34 | 3.04 | 2.93 | 5.00 | 2.75 |
| 35 | 2.79 | 2.96 | 3.90 | 2.72 |
| 36 | 3.04 | 2.16 | 4.20 | 2.93 |
| 37 | 2.65 | 3.59 | 3.52 | 3.04 |
| 38 | 1.94 | 4.40 | 4.03 | 5.60 |
| 39 | 1.69 | 1.69 | 4.22 | 5.28 |
| 40 | 2.67 | 1.85 | 1.94 | 2.25 |
| Mean | 2.61 | 3.32 | 4.03 | 3.88 |

** drop out, therefore no data available

The study clearly shows that significant whitening in tooth colour was obtained by the product of the invention. Already after the first application, visual tooth whitening (ΔE>3) occurred for a lot of the patients. On average, a visual whitening effect was seen after D1. Further improvement occurred after a week of daily treatment at home. Of note, the whitening effect of treatment occurred for all patients, with varying degree. Even after 30 days, the whitening effect was still detectable for most subjects.

Of note, most patients did not have homogenous discolorations or yellowing of teeth. The effects of the composition of the invention on single teeth with previous darker colour were more pronounced than the effects seen in the mean values.

The mean degree of tooth whitening is comparable to state of the art chemical bleaching methods (e.g., leading to ΔE of ΔE of less than 4 for home bleaching, ΔE of about 2.4-5.7 after 7 days, or 2.9-5.5 after 14 days for whitening strips, and up to ΔE 12 for power bleachings (in-office use only) (Gerlach et al., 2002; Demarco et al., 2009; Delfino et al., 2009.)

However, the dental care product and method of the invention has significant advantages over chemical bleaching with regard to undesired effects such as tooth erosion, increased tooth sensitivity etc.

LITERATURE

Dabanoglu et al., 2009, Am J Dent 22:23-29.
Dahl et al., 2003, Crit Rev Oral Biol Med 14(4):292-304.
Delfino et al., 2009, J Appl. Oral Sci 17(4):284-8.
Demarco et al., 2009. Braz Oral Res. 23 Suppl 1:64-70.
Gerlach et al., 2002. Am J Dent. 15 Spec No:7A-12A.
Jiang et al, 2008, J Dent 36(11): 907-914.
Jin et al., 2013, Eur I Oral Sci 121: 382-388.
Lim et al., 2009, Biomed Mater 4(2): 025017.
Mohd et al., 2007, Biomed Mater Eng 17(2): 69-75.
Niwa et al. J Mater Sci Mater Med 2001; 12: 277-281.
Raoufi, S. and D. Birkhed (2010). Int Dent J60(6): 419-423.
Roveri, Battistelli et al., 2009, J Nanomaterial, special issue, Article ID 746383 EP 1 762 215 A1, EP 2 327 428 A2 US 20050037948 A1, US 20080075675 A1, US 2008199431 A1, US 20100247589 A1, US 20100297203 A1, US 2010/0247457 A1
U.S. Pat. No. 6,548,630
WO 2004/007532 A1, WO 2006/073889 A2, WO 2007/000979 A1, WO 2006/047315 A2, WO 2007/137606 A1, WO 2008/113030 A2, WO 2009/026729 A1, WO 2010/
041636 A1, WO 2010/103887 A1, WO 2013/068020 A1,
WO2010/019651 A1

JP2008/081424, JPH115722
JPH115722, JP2008/081424, JP 2007/0176862, JP 2001/
131041, CN101385856

The invention claimed is:

1. A dental care product comprising 0.4-40 wt % calcium phosphate particles and 0.001-5 wt % of a self-assembled protein forming a hydrogel, wherein the particles have a size of 0.01-50 µm, wherein the self-assembled protein comprises the amino acid sequence SEQ ID NO: 1.

2. The dental care product of claim 1, wherein said calcium phosphate particles comprise hydroxyapatite.

3. The dental care product of claim 1, wherein the dental care product is selected from the group consisting of toothpaste, prophylactic paste, tooth powder, tooth polish, tooth gel, chewing gum, candy, lozenge, mouthwash, whitening strip, coated dental floss, coated toothbrush, paint-on gel, varnish, veneer, and tube, syringe or dental tray comprising a gel or paste.

4. The dental care product of claim 1, comprising 0.5-40 wt % of said calcium phosphate particles and 0.02-1 wt % of said protein, wherein the dental care product is a toothpaste or gel.

5. The dental care product of claim 1, wherein 30-70% of said calcium phosphate particles have a size of 200-600 nm.

6. The dental care product of claim 1, wherein the product comprises hydrogenated starch hydrolysate, aqua, hydrated silica, PEG-8, cellulose gum, sodium monofluorophosphate, aroma, sodium saccharin, citric acid, sodium hydroxide, dicalcium phosphate, self-assembling peptide having the amino acid sequence SEQ ID NO: 1, calcium glycerophosphate, sodium chloride, sodium sulfate, limonene, cinnamal, CI 42090, and added hydroxyapatite particles.

7. The dental care product of claim 1, wherein said particles have a size of 1-25 μm.

8. The dental care product of claim 1, wherein said particles have a size of 4-20 μm.

9. The dental care product of claim 4, comprising 0.5-40 wt % of said calcium phosphate particles and 0.05 wt % of said protein, wherein the dental care product is a toothpaste or gel.

10. The dental care product of claim 4, wherein the dental care product is coated on dental floss or a toothbrush.

11. A method for treating a sensitive tooth, prevention or treatment of caries, tooth whitening, or any combination thereof, comprising administering the dental care product of claim 1 to a tooth in need thereof.

12. The method of claim 11, wherein the composition is administered one, two or three times a day on 1, 2, 3, 4, 5, 6, 7 or more days.

* * * * *

```
                               SEQUENCE LISTING

<160> NUMBER OF SEQ ID NOS: 19

<210> SEQ ID NO 1
<211> LENGTH: 11
<212> TYPE: PRT
<213> ORGANISM: Artificial Sequence
<220> FEATURE:
<223> OTHER INFORMATION: self-assembling peptide

<400> SEQUENCE: 1

Gln Gln Arg Phe Glu Trp Glu Phe Glu Gln Gln
1               5                   10

<210> SEQ ID NO 2
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 2

Gln Gln Xaa Phe Xaa Trp Xaa Phe Gln Gln Gln
1               5                   10

<210> SEQ ID NO 3
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 3

Gln Gln Arg Phe Xaa Trp Xaa Phe Glu Gln Gln
1               5                   10

<210> SEQ ID NO 4
<211> LENGTH: 11
<212> TYPE: PRT
<213> ORGANISM: Artificial Sequence
<220> FEATURE:
<223> OTHER INFORMATION: self-assembling peptide

<400> SEQUENCE: 4

Gln Gln Arg Phe Gln Trp Gln Phe Glu Gln Gln
1               5                   10
```

```
<210> SEQ ID NO 5
<211> LENGTH: 11
<212> TYPE: PRT
<213> ORGANISM: Artificial Sequence
<220> FEATURE:
<223> OTHER INFORMATION: self-assembling peptide

<400> SEQUENCE: 5

Gln Gln Glu Phe Glu Trp Glu Phe Glu Gln Gln
1               5                   10

<210> SEQ ID NO 6
<211> LENGTH: 10
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (9)..(9)
<223> OTHER INFORMATION: Orn

<400> SEQUENCE: 6

Gln Gln Xaa Phe Xaa Trp Xaa Phe Xaa Gln
1               5                   10

<210> SEQ ID NO 7
<211> LENGTH: 11
<212> TYPE: PRT
<213> ORGANISM: Artificial Sequence
<220> FEATURE:
<223> OTHER INFORMATION: self-assembling peptide

<400> SEQUENCE: 7

Glu Gln Glu Phe Glu Trp Glu Phe Glu Gln Glu
1               5                   10

<210> SEQ ID NO 8
<211> LENGTH: 11
<212> TYPE: PRT
<213> ORGANISM: Artificial Sequence
<220> FEATURE:
<223> OTHER INFORMATION: self-assembling peptide

<400> SEQUENCE: 8

Gln Gln Glu Phe Glu Trp Glu Phe Glu Gln Gln
1               5                   10

<210> SEQ ID NO 9
<211> LENGTH: 11
<212> TYPE: PRT
<213> ORGANISM: Artificial Sequence
<220> FEATURE:
<223> OTHER INFORMATION: self-assembling peptide

<400> SEQUENCE: 9

Glu Ser Glu Phe Glu Trp Glu Phe Glu Ser Glu
1               5                   10
```

-continued

```
<210> SEQ ID NO 10
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (9)..(9)
<223> OTHER INFORMATION: Orn

<400> SEQUENCE: 10

Gln Gln Xaa Phe Xaa Trp Xaa Phe Xaa Gln Gln
1               5                   10

<210> SEQ ID NO 11
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (9)..(9)
<223> OTHER INFORMATION: Orn
<220> FEATURE:
<221> NAME/KEY: MOD_RES
<222> LOCATION: (11)..(11)
<223> OTHER INFORMATION: Orn

<400> SEQUENCE: 11

Xaa Gln Xaa Phe Xaa Trp Xaa Phe Xaa Gln Xaa
1               5                   10

<210> SEQ ID NO 12
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (3)..(3)
<223> OTHER INFORMATION: Orn
```

```
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (9)..(9)
<223> OTHER INFORMATION: Orn

<400> SEQUENCE: 12

Ser Ser Xaa Phe Xaa Trp Xaa Phe Xaa Ser Ser
1               5                   10

<210> SEQ ID NO 13
<211> LENGTH: 11
<212> TYPE: PRT
<213> ORGANISM: Artificial Sequence
<220> FEATURE:
<223> OTHER INFORMATION: self-assembling peptide

<400> SEQUENCE: 13

Ser Ser Arg Phe Glu Trp Glu Phe Glu Ser Ser
1               5                   10

<210> SEQ ID NO 14
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 14

Ser Ser Arg Phe Xaa Trp Xaa Phe Glu Ser Ser
1               5                   10

<210> SEQ ID NO 15
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (9)..(9)
<223> OTHER INFORMATION: Orn
```

```
<400> SEQUENCE: 15

Gln Gln Xaa Phe Xaa Trp Xaa Phe Xaa Gln Gln
1               5                   10

<210> SEQ ID NO 16
<211> LENGTH: 11
<212> TYPE: PRT
<213> ORGANISM: Artificial Sequence
<220> FEATURE:
<223> OTHER INFORMATION: self-assembling peptide

<400> SEQUENCE: 16

Asn Asn Arg Phe Glu Trp Glu Phe Glu Asn Asn
1               5                   10

<210> SEQ ID NO 17
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 17

Asn Asn Arg Phe Xaa Trp Xaa Phe Glu Asn Asn
1               5                   10

<210> SEQ ID NO 18
<211> LENGTH: 11
<212> TYPE: PRT
<213> ORGANISM: Artificial Sequence
<220> FEATURE:
<223> OTHER INFORMATION: self-assembling peptide

<400> SEQUENCE: 18

Thr Thr Arg Phe Glu Trp Glu Phe Glu Thr Thr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 19

Thr Thr Arg Phe Xaa Trp Xaa Phe Glu Thr Thr
1               5                   10
```